United States Patent [19]

Lee

[11] Patent Number: 5,184,761
[45] Date of Patent: Feb. 9, 1993

[54] DISPENSING APPARATUS

[75] Inventor: Graham S. Lee, Norfolk, United Kingdom

[73] Assignee: Bespak plc, King's Lynn, United Kingdom

[21] Appl. No.: 760,448

[22] Filed: Sep. 17, 1991

[30] Foreign Application Priority Data

Sep. 20, 1990 [GB] United Kingdom ................. 9020555

[51] Int. Cl.$^5$ ............................................ B65D 83/00
[52] U.S. Cl. ................................ 222/402.2; 222/182; 222/183; 222/162; 128/200.23; 239/350; 604/140
[58] Field of Search ............... 222/162, 182, 183, 325, 222/402.2; 604/58, 140; 128/200.23; 239/350

[56] References Cited

U.S. PATENT DOCUMENTS

| 3,157,179 | 11/1964 | Paullus et al. | 222/402.2 X |
| 3,605,738 | 9/1971 | Ciranna | 128/200.23 |
| 3,826,413 | 9/1974 | Warren . | |
| 4,576,157 | 3/1986 | Raghuprasad . | |
| 4,955,371 | 9/1990 | Zamba et al. . | |
| 4,969,578 | 11/1990 | Gander et al. | 222/162 X |
| 5,037,012 | 8/1991 | Langford | 222/402.2 |
| 5,082,149 | 1/1992 | Cross | 222/162 |

FOREIGN PATENT DOCUMENTS 2233236 1/1991 United Kingdom .

Primary Examiner—Gregory L. Huson
Attorney, Agent, or Firm—Beveridge, DeGrandi, Weilacher & Young

[57] ABSTRACT

An inhaler for medical aerosols includes a flow sensor 32 in the form of a piston which is movable against a spring bias 35 in response to inhalation. Movement of the piston unseats a valve member 30 allowing a pressurized dose to be released through a nozzle 67. A uniform impedance to the flow of air is provided throughout the movement of the piston to avoid any discontinuity in the flow. The apparatus is particularly suited for inhalers used in the treatment of asthma.

9 Claims, 5 Drawing Sheets

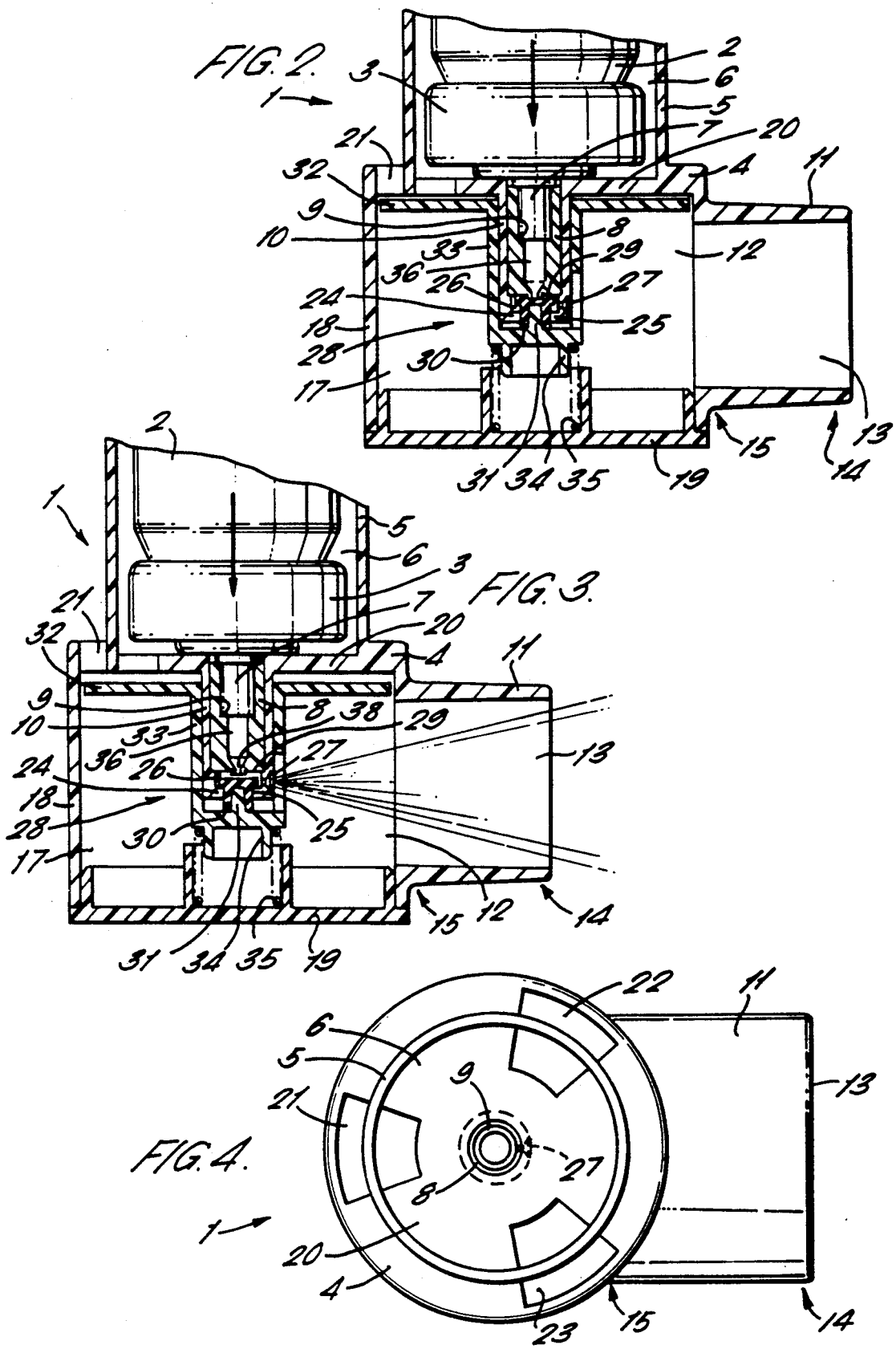

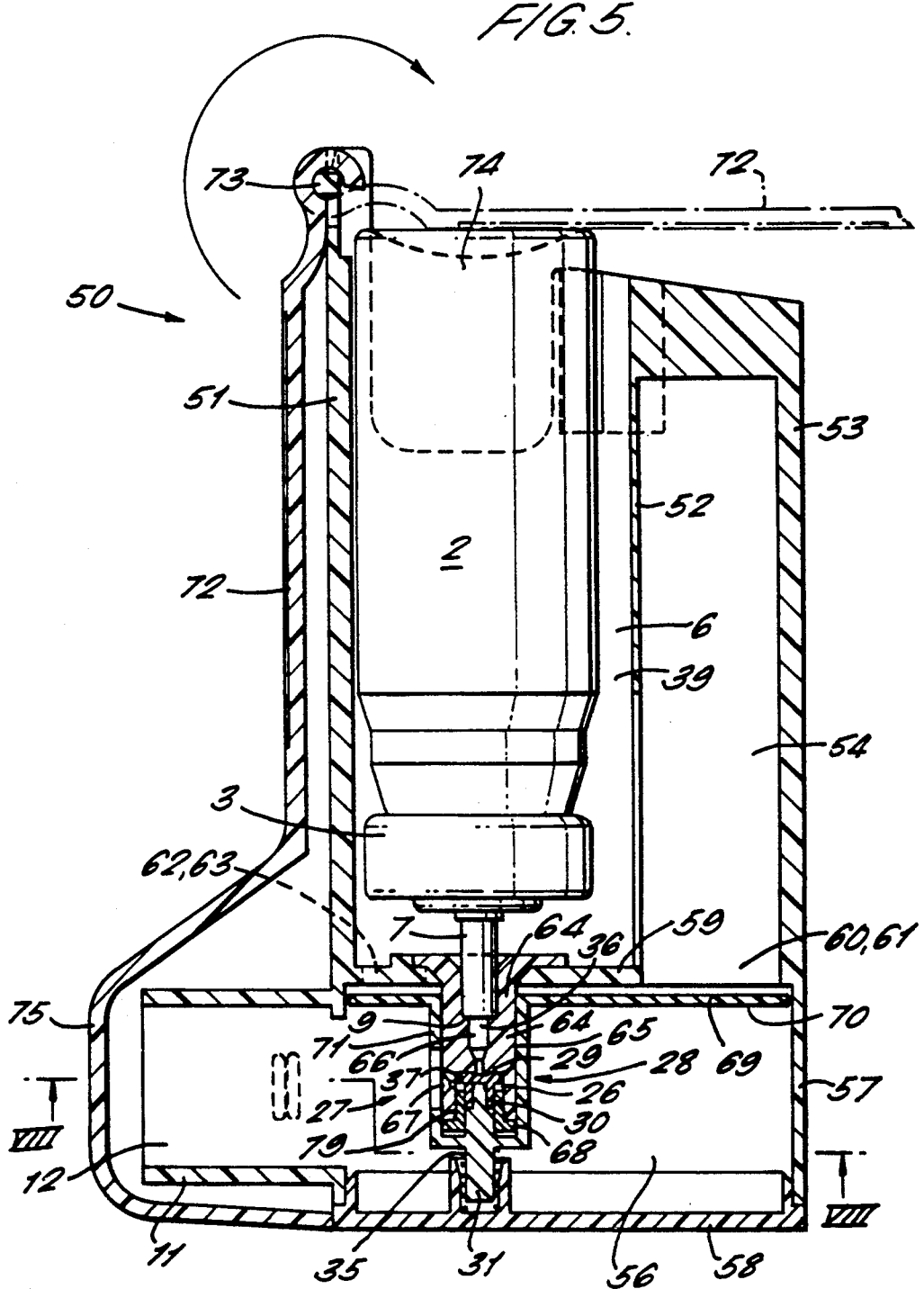

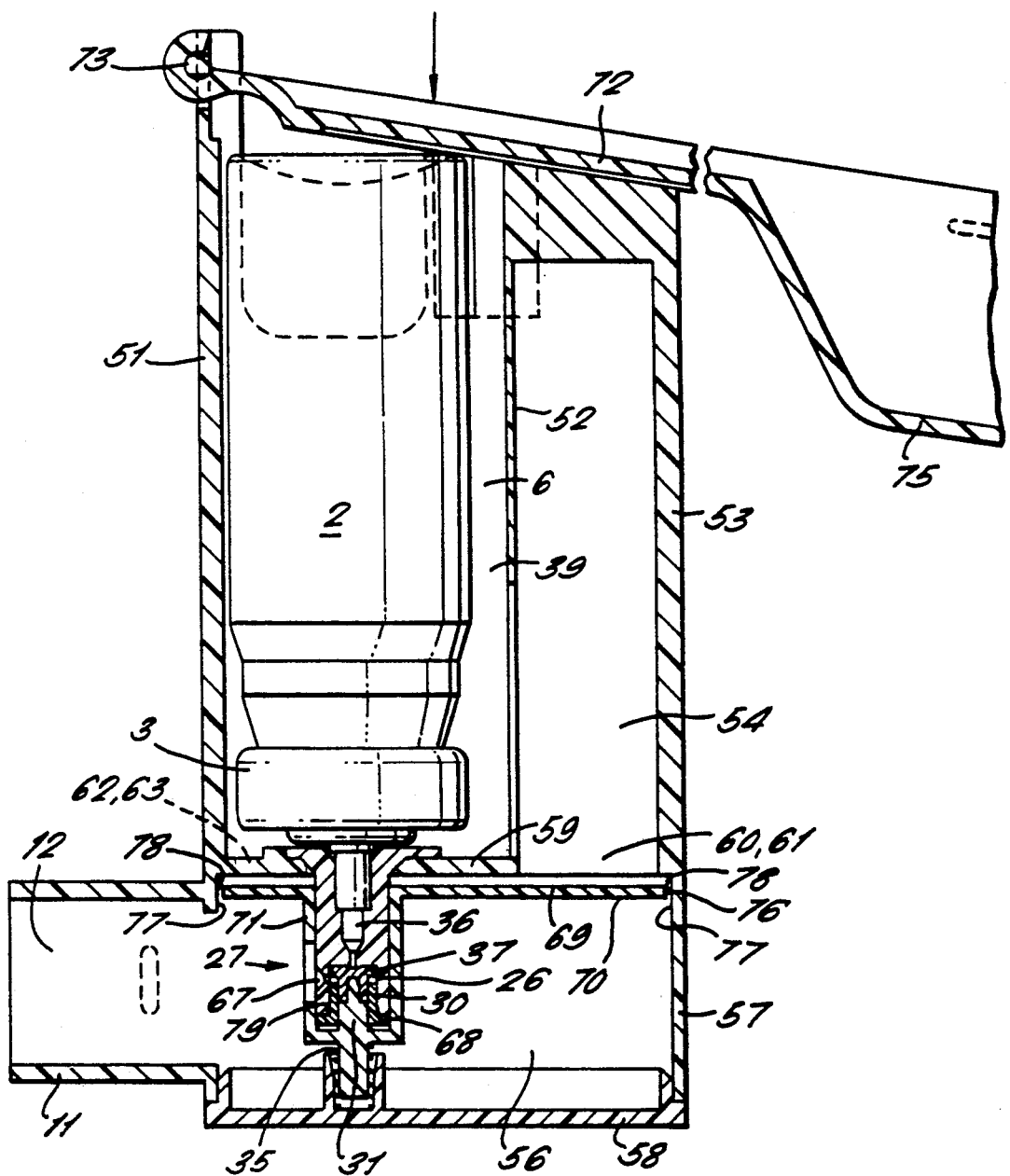

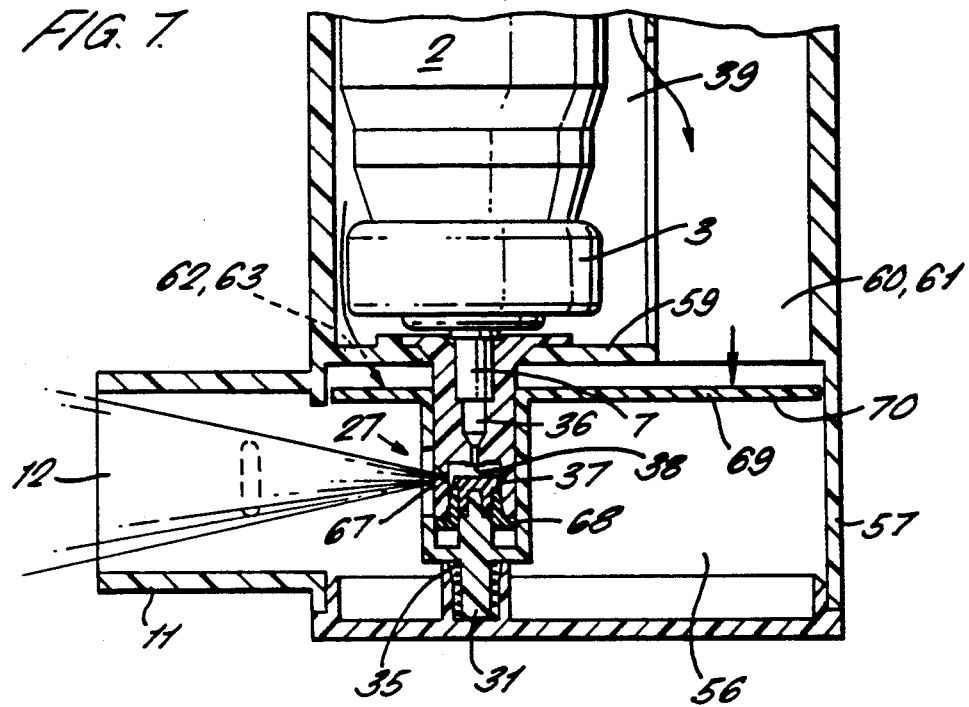
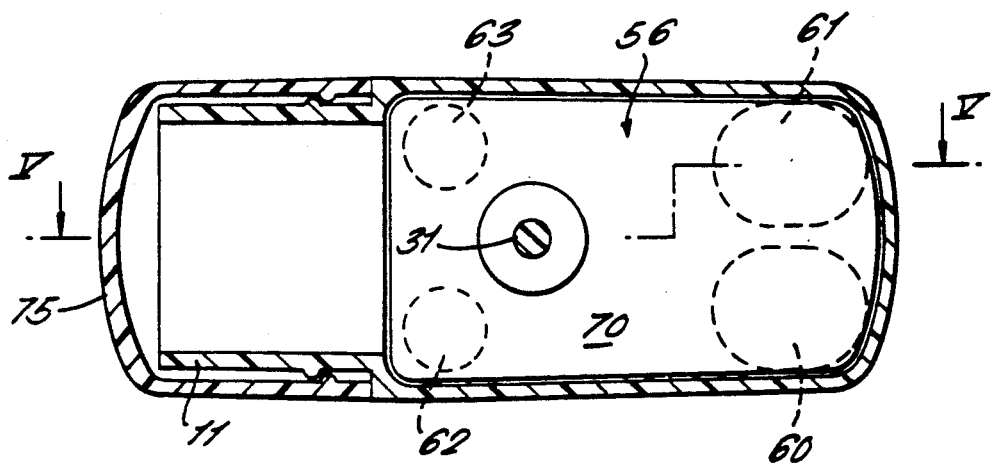

DISPENSING APPARATUS

This invention relates to dispensing apparatus for use with pressurised dispensing containers and in particular but not exclusively for dispensing apparatus for dispensing orally inhaled medicinal products in aerosol form.

Various means have been proposed to synchronise the release of an aerosol product into a mouthpiece of a dispensing apparatus in a manner which is synchronised with the inhalation of breath by a user. Such synchronisation is important in ensuring that as much as possible of the dispensed dose reaches the lungs of the user. This is of particular importance when administering drugs for the relief of asthma.

It is known from GB-1392192 to provide dispensing apparatus comprising a housing defining a socket receiving in use a pressurised dispensing container of the type having a tubular valve stem biassed into an extended position and having first valve means operable to dispense fluid through the stem when the stem is depressed, the housing defining an airway extending from an inlet means open to the atmosphere to an outlet defined by a mouthpiece whereby inhalation of a user results in an air flow through the airway, the apparatus further comprising an actuator in which the stem is sealingly received in use such that the actuator and the stem together define a first chamber into which fluid is dispensable by operation of the first valve means, a second valve means normally closing the chamber and actuatable to release fluid from the first chamber to flow into the airway, the second valve means comprising a valve member located externally of the first chamber and cooperable with a valve seat of the actuator, and a flow sensor arranged in the airway and operable to actuate the second valve means in response to a flow of air being sensed in the airway.

The flow sensor proposed in GB-1392912 is a pivoted vane mechanism which is difficult to manufacture to the required tolerance for controlled and repeatable performance in oral inhalation due to difficulties in moulding and distortions appearing in the moulded elements. This arrangement has therefore not been adopted and there remains a need to provide a practical solution which will be suitable for production on a commercial scale.

According to the present invention a dispensing apparatus is characterised in that the flow sensor comprises a piston which is axially movable in response to the flow of air in a bore defined by the housing between first and second positions corresponding to closed and open conditions of the second valve means respectively, the piston being connected directly to the valve member and provided with biassing means urging the piston into the first position in which the valve member is biassed into sealing contact with the valve seat.

An advantage of such an arrangement is that it has been found to be more readily manufacturable using moulded plastics materials without the tolerance and distortion problems associated with prior art devices.

A further advantage of the present invention is that the direct connection between the piston and the valve member simplifies the construction and improves the operating efficiency of the apparatus.

Preferably the piston is provided with guide means operable to guide the movement of the piston so as to maintain a lateral surface of the piston in spaced relationship from a side wall of the bore to thereby define a passageway therebetween having a cross-section which is substantially uniform throughout the travel of the piston between the first and second positions, the passageway constituting a constricted portion of the airway which presents a substantially uniform impedance to the flow of air throughout the movement of the piston.

An advantage of this arrangement is that the user experiences a constant impedance to the inhaled air flow throughout the inhalation process resulting in a slow and steady flow of air in which the atomised medicament is carried. Such a characteristic of flow rate has proved to be highly beneficial to the effective deposition of inhaled medicaments where deposition of an atomised spray in the user's lungs is intended. In contrast, any discontinuity in the flow rate resulting from a change in impedance can result in a rapid increase in flow rate with consequent early deposition of the medicament in the throat or mouth of the user. A further advantage is that the uniformity of flow avoids any "dead spot" in the flow characteristic during which the user is prevented from receiving inhaled air, thereby avoiding unnecessary distress for the user who may for example be an asthmatic.

Advantageously the actuator forms a projection extending into a duct constituting a portion of the airway communicating with the outlet, the piston comprising a tubular guide portion which is axially slidable on a guide surface of the projection to facilitate movement between the first and second positions.

This is particularly convenient since it is necessary for the actuator to project into the duct in order to suitably locate the nozzle in the airway and the existence of this projection can be utilised to provide a guide for the piston without the need for a separate guiding structure.

Preferably the actuator defines a second chamber communicating with the first chamber through a port defined by the valve seat and further defining an outlet nozzle for the release of fluid into the airway, the valve member being located within the second chamber and mounted on a spigot portion of the piston.

An advantage of this arrangement is that the nozzle provides a directional atomised spray of fluid which conveniently can be directed into the mouthpiece for inhalation.

Conveniently the spigot projects into the second chamber through an aperture defined in an end wall of the actuator, the valve member being urged into sealing contact with the end wall to seal the aperture by movement of the piston into the second position.

Preferably the valve member comprises a body portion connected to the spigot so as to extend through the aperture in the end wall of the actuator and a head portion making sealing contact with the valve seat in the first position of the piston, the head portion being of greater cross-section than the aperture and comprising a peripheral flange operable to make sealing contact with the end wall in the second position of the piston.

An advantage of this arrangement is that the flange positively retains the head of the valve member within the second chamber.

Preferably the valve member is connected to the spigot by connection means operable to urge the valve member away from the valve seat during motion of the piston from the first position to the second position.

An advantage of this arrangement is that the valve member is positively unseated from the valve seat to thereby overcome any tendency for the valve member to stick in the sealing position.

Conveniently the airway extends through the socket and the housing defines at least one port communicating between the socket and the duct at a location upstream of the piston with respect to the direction of air flow during inhalation.

Advantageously the housing defines a further chamber forming part of the airway and communicating with the socket, the housing defining at least one further port communicating between the further chamber and the duct at a location upstream of the piston with respect to the direction of air flow during inhalation.

Preferably the inlet means comprises an aperture defined by the open end of the socket.

An advantage of this arrangement is that this provides a large cross-section air intake at a location which will not readily be obstructed by the user's fingers which could otherwise constrict the inflow of air to the apparatus.

Embodiments of the present invention will now be described by way of example only and with reference to the accompanying drawings of which:

FIG. 2 is a sectional elevation of the dispensing apparatus of FIG. 1 in which the pressurised dispensing container has been depressed to actuate a first valve means;

FIG. 3 is a sectional elevation of the dispensing apparatus of FIG. 1 in which dispensed fluid is released into a flow of inhaled air;

FIG. 4 is a plan view of the dispensing apparatus of FIGS. 1 to 3 without a pressurised dispensing container;

FIG. 5 is a sectioned elevation of an alternative dispensing apparatus;

FIG. 6 is a sectioned elevation of the apparatus of FIG. 5 in which the pressurised dispensing container has been depressed to actuate a first valve means;

FIG. 7 is a sectional elevation of the apparatus of FIGS. 5 and 6 in which the dispensed fluid is released into a flow of inhaled air; and FIG. 8 is a plan sectional view of the dispensing apparatus of FIGS. 5, 6 and 7 sectioned at VIII of FIG. 5.

Figure 1:
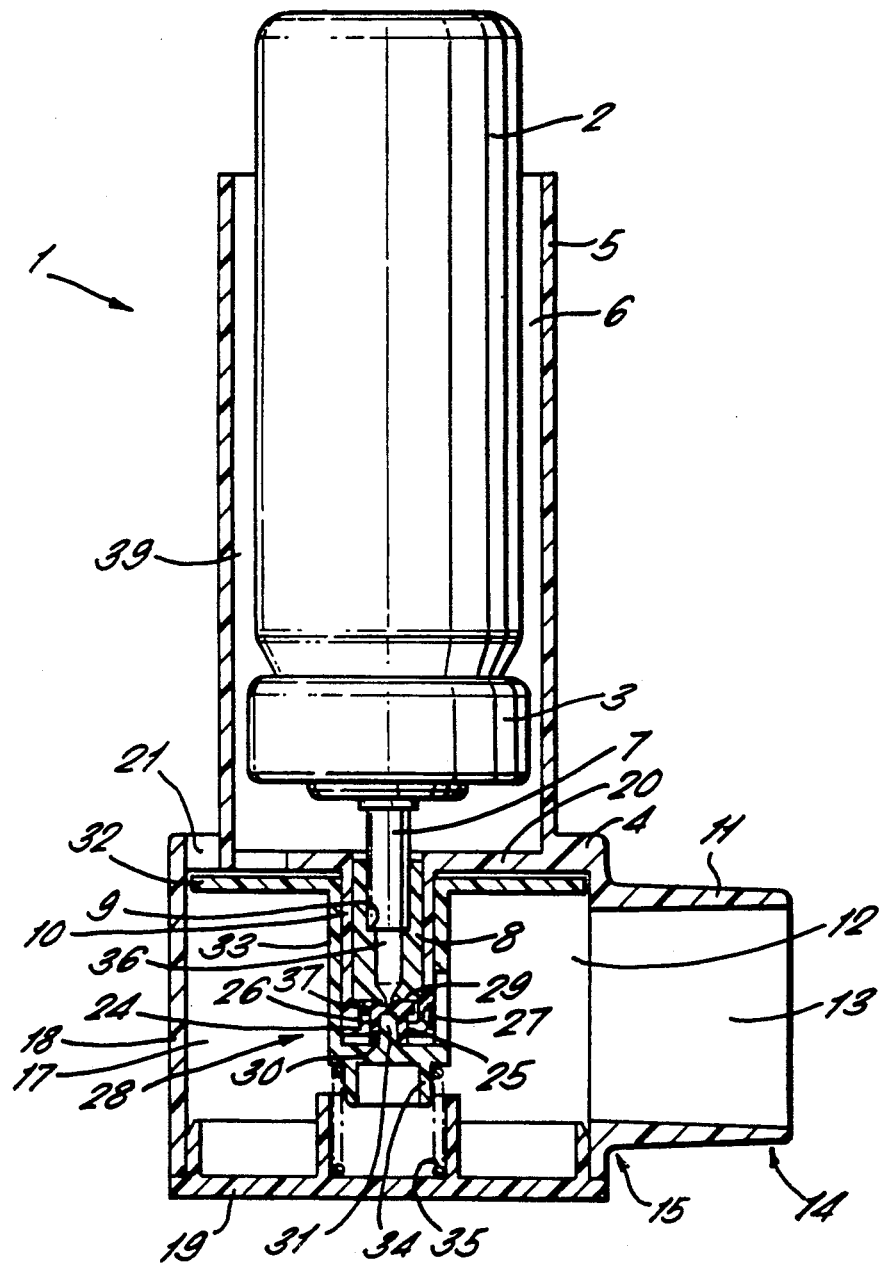
FIG. 1 is a sectional elevation of a dispensing apparatus in accordance with the present invention and including a pressurised dispensing container.

In FIG. 1 a dispensing apparatus 1 is shown in combination with a pressurised dispensing container 2 with the apparatus oriented so as to be ready for use in an orientation in which the pressurised dispensing container extends vertically with a first valve means 3 lowermost. The pressurised dispensing container 2 contains a liquid medicament mixed with a volatile propellant liquid.

In the following description the reference to vertical and horizontal orientation of components of the apparatus 1 refer to orientations of such components when the apparatus is held in its normal working orientation shown in FIG. 1.

The apparatus comprises a housing 4 which includes an upwardly projecting cylindrical portion 5 defining a cylindrical recess or socket 6 in which the container 2 is axially and slidably received. The container 2 is a loose fit in the socket 6 such that air can freely flow through the socket through a peripheral space 39 between the container and the socket.

A valve stem 7 projects downwardly from the pressurised dispensing container 2. The first valve means 3 which is located internally of the pressurised dispensing container 2 is actuated by axial depression of the valve stem 7 against internally provided spring bias to dispense a metered dose of fluid through the tubular valve stem.

The valve stem 7 is received sealingly in a tubular actuator 8 which defines an annular shoulder 9 which acts as a stop limiting the extent to which the valve stem 7 extends within the actuator 8.

The actuator 8 is received as a snug fit within a downwardly extending tubular projection 10 formed integrally with the housing 4.

The housing 4 further comprises a mouthpiece 11 defining a horizontally extending air duct 12 communicating with an outlet orifice 13 at a first end 14 of the mouthpiece. A second end 15 of the mouthpiece 11 communicates with a lower chamber formed by a bore 17 defined by an axially vertical cylindrical wall 18 of the housing 4.

The bore 17 is closed by a lower disc portion 19 and an upper disc portion 20 of the housing 4 such that the upper disc portion 20 forms a lower end wall of the cylindrical portion 5. The upper disc portion 20 is provided with three circumferantially equispaced inlet ports 21, 22 and 23 allowing air to enter the bore 17 partly from the peripheral space 39 in the socket 6 and partly from the exterior of the housing. The outlet orifice 13 is of oval cross-section so as to be comfortably received in the mouth of a user.

The air duct 12 extends from the inlet ports 21, 22 and 23 through the bore 17 and the mouthpiece 11 to the outlet orifice 13.

The tubular projection 10 has a lower end wall 24 defining an aperture 25 communicating with an annular space 26 formed between the lower end wall and the actuator 8. A nozzle 27 defined by the tubular projection 10 communicates with the annular space 26 and is oriented to release fluid from the annular space into the bore 17 in a direction towards the outlet orifice 13.

A second valve means 28 is formed in the tubular projection 10 by an annular valve seat 29 at the lower end of the actuator 8 and a resilient valve member 30 which extends from the bore 17 into the annular space 26 and is normally urged into sealing contact with the valve seat 29 by a spigot 31. The valve member 30 has a cylindrical body which is recessed to accommodate the spigot 31 as an interference fit so that the spigot and valve member are connected sufficiently firmly to enable the valve member to be positively unseated from the valve seat when the spigot is retracted. The valve member 30 is recessed so as to be penetrated by the spigot 31 which is received as an interference fit thereby firmly attaching the valve member to the spigot. The valve member 30 is a sliding fit within the aperture 25 and is provided with a radially projecting flange 37 of greater diameter than the aperture 25 so that the flange acts as a stop limiting downward motion of the valve member 30 through the aperture.

A piston 32 is vertically slidably received in the cylindrical bore 17 and includes a tubular guide 33 which is axially slidably mounted on the tubular projection 10. A boss 34 projects downwardly from the guide 33 and a helical compression spring 35 is located on the boss 34 and extends into contact with the lower disc portion 19 so as to bias the piston 32 upwardly. The spigot 31 is connected rigidly to the piston 32 so that the upward bias provided by the spring 35 urges the spigot upwardly to thereby bias the resilient valve member 30 into sealing contact with the valve seat 29. The second valve means 28 is thereby normally held in a closed condition.

The piston 32 is shown in FIGS. 1 and 2 in its normal rest position in which it lies adjacent the lower disc portion 19 of the housing 4 and is a loose fit in the bore 5 so as to allow a restricted flow of air from the inlet ports 21, 22 and 23 into the cylindrical bore 17. The piston 32 is of 30.8 mm diameter and the bore 17 is dimensioned to provide a clearance of 0.35 mm between each side of the piston and bore. A restricted annular air passageway is thereby defined between the piston 32 and the bore 17. The ports 21, 22 and 23 are in contrast dimensioned to provide a greater cross-sectional area for the passage of air.

The actuator 8 and the hollow tubular valve stem 7 together define a first chamber 36 which is normally closed at its upper end by the first valve means 3 and at its lower end by the second valve means 28.

In use a user holds the housing 4 with the cylindrical portion 5 vertical as illustrated in FIGS. 1 to 4 and inserts the mouthpiece 11 into the user's mouth. The user also depresses the pressurised dispensing container 2 relative to the housing 4 so as to actuate the first valve means 3 by relative movement between the container 2 and the valve stem 7 which is prevented from downward movement by abutment with the annular shoulder 9 in the actuator 8.

Actuation of the first valve means 3 results in a pressurised metered dose of fluid entering the first chamber 36 from which it is prevented from escaping by the second valve means 28. The user then inhales orally through the mouthpiece 11 thereby reducing air pressure within the bore 17. The piston 32 is subjected to a downward force because of an imbalance of air pressure above and below the piston since the air pressure above the piston is maintained at ambient air pressure via the inlet ports 21, 22 and 23. The piston is thereby urged downwardly against the spring pressure provided by spring 35. As the piston 32 moves downwardly the spigot 31 also moves downwardly thereby unseating the resilient valve member 30 from the valve seat 29 so that the pressurised fluid escapes from the first chamber 36 into the annular space 26 which constitutes a second chamber. As fluid begins to escape, dissolved propellant in liquid form boils off from the dispensed dose causing the escaping fluid to rapidly expand. This expansion assists in further displacing the valve member 30 away from the seat 29. Displacement of the valve member 30 away from the seat is limited by engagement between the flange 37 and the lower end wall 24 of the tubular projection 10. Fluid pressure acting on the valve member 30 provides sealing action between the flange 37 and the lower end wall 24 so that pressurised fluid cannot escape through the aperture 25. The pressurised fluid within the second chamber i.e. annular space 26 then escapes via the nozzle 27 as shown in FIG. 3. The piston 32 thereby constitutes a flow sensor which detects the flow of air in the duct 12 and which enables the second valve means 28 to be actuated to dispense the metered dose in synchronisation with the inhalation of breath.

Air is drawn during inhalation through the air duct 12 via the inlet ports 21, 22, 23 and passes peripherally around the piston 32 into the bore 17 and thereafter is inhaled through the mouthpiece 11. Fluid dispensed through the nozzle 27 is mixed with the inhaled air and is administered to the lungs of the user.

Release of manual pressure on the pressurised dispensing container 2 allows the container to resume its normal position as shown in FIG. 1 and at the end of inhalation the piston 32 returns to its rest position as shown in FIG. 1 by action of the spring 35. The dispensing apparatus 1 is then ready for re-use.

The mouthpiece may be provided with a cap (not shown) to prevent the ingress of debris when the apparatus 1 is not in use.

An alternative dispensing apparatus 50 will now be described with reference to FIGS. 5, 6, 7 and 8 using corresponding reference numerals to those of the preceding Figures where appropriate for corresponding elements.

Apparatus 50 is shown in combination with a pressurised dispensing container 2 with the apparatus oriented so as to be ready for use in an orientation in which the pressurised dispensing container extends vertically with a first valve means 3 lowermost.

The apparatus 50 has a housing 51 with an upright tubular portion 52 defining a recess or socket 6 in which a pressurised dispensing container 2 is axially and slidably received.

The housing 51 also includes a lateral extension 53 defining an elongate chamber 54 extending parallel to the socket 6. An opening 55 communicates between the socket 6 and the elongate chamber 54. The housing further comprises a mouthpiece 11 defining a horizontally extending air duct 12 communicating with a lower chamber 56. The lower chamber 56 is formed by an upright tubular portion 57 having a generally rectangular cross-section as seen in FIG. 8, the lower chamber 56 being closed by a lower end wall 58 of the housing 51 and separated from the socket 6 by an upper end wall 59.

FIG. 5 is a staggered sectional elevation taken along V—V of FIG. 8.

Left and right-hand ports 62 and 63 are provided in the upper end wall 56 so as to communicate directly between the lower chamber 56 and the recess 6.

Further left and right-hand ports 60 and 61 are provided in the upper end wall 59 so as to communicate between the lower chamber 56 and the elongate chamber 54.

The container 2 of the apparatus 50 includes a first valve means 3 and a valve stem 7 of the type referred to with reference to apparatus 1, the valve stem being received sealingly in a tubular actuator 64 which defines an annular shoulder 9 acting as a stop which limits the extent to which the valve stem 7 extends within the actuator.

The actuator 64 projects downwardly from the upper end wall 59 and has a cylindrical external surface 65.

The actuator 64 is generally tubular having an axial bore 66 which is stepped in diameter to define a valve seat 29 which is normally engaged by a valve member 30 of the type referred to above with reference to the apparatus 1. A radial bore 67 formed in the actuator 64 provides a nozzle 27 which is directed into the air duct in the direction of the mouthpiece 11. The valve member 30 normally is maintained in sealing contact with the valve seat 29 thereby constituting a second valve means 28. The actuator 64 and the hollow tubular valve stem 7 together define a first chamber 36 which is normally closed at its upper end by the first valve means 3 and at its lower end by the second valve means 28. The valve member 30 is maintained at its normal sealing position by a spigot 31 which is upwardly biassed by means of a helical compression spring 35 connected to the lower end wall 56.

The nozzle 27 communicates via the radial bore 67 with an annular space constituting a second chamber 26 into which the valve member 30 projects from a tubular insert 68 received within an axial bore 79 such that the spigot 31 and the valve member 30 are a sliding fit therein.

The valve member 30 includes a radially projecting flange 37 which limits downward motion of the valve member relative to the insert 68 and provides sealing contact between the valve member and the insert when the valve member is moved downwardly to its fullest extent away from the valve seat 29.

The spigot 31 is formed unitarily with a piston 69 having a generally rectangular face portion 70 which is connected to the spigot by a tubular guide portion 71. The guide portion 71 is received as a sliding fit on the actuator 64 and is slidable on the cylindrical external surface 65. The compression spring 35 acts upwardly on the guide portion 71. The piston 69 has a lateral surface 76 which is spaced from a side wall 77 of the lower chamber 56 to define an annular passageway 78. The side wall 77 is shaped to have a uniform separation from the lateral surface 76 around the entire periphery of the piston 69 and also throughout the available travel of the piston between a first position shown in FIG. 6 in which the piston is uppermost and a second position shown in FIG. 7 in which the piston is lowermost. The spacing between the face portion 70 and the upper end wall 59 when the piston is in the first position is 1.05 mm which is greater than the separation between the lateral surface 76 and side wall 77 which is 0.37 mm. This ensures that there is no significant impedance to air flow resulting from any constriction between the face portion 70 and the upper end wall 59.

As shown in FIG. 5, the housing is provided with a lever 72 which is pivotally connected to the housing by a hinge 73 which is located adjacent to an upper end portion 74 of the container 2. The lever 72 includes a cover portion 75 which in the position shown in FIG. 5 fits over and encloses the mouthpiece 11. The lever 72 can be pivoted to a second position shown in chain dot in FIG. 5 in which the mouthpiece 11 is uncovered and the lever rests in contact with the upper end portion 74. The lever 72 is further pivotable from this second position to a third position shown in FIG. 6 in which the container 2 is moved axially by action of the lever in a downward direction towards the actuator 64 so as to provide relative movement between the valve stem 7 and the first valve means 3.

In use the user moves the lever 72 into the position shown in chain dot in FIG. 5 in which the mouthpiece 11 is uncovered and the lever makes contact with the upper end portion of the pressurised dispensing container. Mouthpiece 11 is then inserted into the user's mouth and the housing is held in an orientation in which the tubular portion 52 extends vertically as shown in FIG. 5. Lever 72 is then manually depressed so as to move pivotally about hinge 73 and translate the container 2 towards the actuator 64. This movement actuates the first valve means 3 by relative movement between the container 2 and the valve stem 7 which is prevented from downward movement by abutment with the annular shoulder 9 in the actuator 64.

The piston 69 is initially in its first position as shown in FIGS. 5 and 6 in which the spigot 31 urges the valve member 30 to its greatest extent into sealing contact with the valve seat 29. The second valve means 28 is therefore closed.

After initially being unseated the movement of the valve member is assisted by pressure from the escaping fluid which expands rapidly due to boiling off of propellant vapour.

Actuation of the first valve means 3 results in a pressurised metered dose of fluid entering the chamber 36 from which it is prevented from escaping by the second valve means 28. The user then inhales orally through the mouthpiece 11 and a flow of air passes through the air duct 12 from the socket 6 via ports 62 and 63 and also via ports 60 and 61 through the elongate chamber 54. The flow of air passes peripherally around the face portion 70 of the piston 69 through passageway 78. The relatively constricted cross-section of flow through the passageway 78 results in a pressure differential being created across the face portion 70 of the piston thereby urging the piston downwardly against the spring bias provided by the spring 35 and thereby moving the spigot 31 away from the actuator 64. This motion opens the second valve means by unseating the valve member 30 which travels away from the valve seat 29 so as to come to rest in a position in which the flange 37 makes sealing contact with the insert 69. In this second position of the piston 69 the fluid within the chamber 36 is free to escape from the first chamber 36 into the annular space of the second chamber 26. As fluid begins to escape dissolved propellant in liquid form boils off from the dispensed dose causing the escaping fluid to rapidly expand. The pressurised fluid then escapes through the nozzle 27 as illustrated in FIG. 7 and the liquid dose is atomised by the nozzle 27 to be entrained in the air flow which is orally inhaled The lever 72 is then released and the container 2 returns to its original position under spring action provided by the first valve means 3.

Throughout the above procedure the apparatus 50 is held in one hand by the user with the user's fingers engaging the lower part of the housing. Since the inflow of air to the apparatus 50 is entirely through the open upper end of the socket 6 there is no obstruction to the air flow by the user's fingers.

The apparatus 1 or 50 may also optionally include a mechanism for retaining the container 2 in its depressed condition throughout the dispensing operation. This is advantageous where the first valve means 3 is of a type which vents to atmosphere the internal bore of the valve stem when the first valve means is in the closed condition. It is therefore important for the container 2 to remain depressed relative to the housing 4 until after the second valve means has been actuated to dispense the dose into the inhaled air.

The apparatus 50 may be modified to be manually operated by depression of the container 2 i.e. without having a lever 72 and may then be provided with a separate cap for preventing ingress of dust to the socket 6.

The wide wall 77 on lateral surface 76 of the piston 69 may be provided with a localised projection which locally varies the size of passageway 78. This would be useful in fine tuning the overall cross-sectional area of the passageway 78 and would enable the area to be modified without re-configuring the entire piston 69. Typical dimensions for a practical device would prove a bore area of 965 square mm and a piston area of 925 mm, giving a passageway of 40 square mm.

I claim:

1. Dispensing apparatus comprising a housing defining a socket receiving in use a pressurised dispensing container of the type having a tubular valve stem biassed into an extended position and having first valve means operable to dispense fluid through the stem when the stem is depressed, the housing defining an airway extending from an inlet means open to the atmosphere to an outlet defined by a mouthpiece whereby inhalation of a user results in an air flow through the airway, the apparatus further comprising an actuator in which the stem is sealingly received in use such that the actuator and the stem together define a first chamber into which fluid is dispensable by operation of the first valve means, a second valve means normally closing the first chamber and actuatable to release fluid from the first chamber to flow into the airway, the second valve means comprising a valve member located externally of the first chamber and cooperable with a valve seat of the actuator, and a flow sensor arranged in the airway and operable to actuate the second valve means in response to a flow of air being sensed in the airway, wherein the flow sensor comprises a piston which is axially movable in response to the flow of air in a bore defined by the housing between first and second positions corresponding to closed and open conditions of the second valve means respectively, the piston being connected directly to the valve member and provided with biassing means urging the piston into the first position in which the valve member is biassed into sealing contact with the valve seat.

2. Apparatus as claimed in claim 1 wherein the piston is provided with guide means operable to guide the movement of the piston so as to maintain a lateral surface of the piston in spaced relationship from a side wall of the bore to thereby define a passageway therebetween having a cross-section which is substantially uniform throughout the travel of the piston between the first and second positions, the passageway constituting a constricted portion of the airway which presents a substantially uniform impedance to the flow of air throughout the movement of the piston.

3. Dispensing apparatus as claimed in claim 2 wherein the actuator forms a projection extending into a duct constituting a portion of the airway communicating with the outlet, the piston comprising a tubular guide portion which is axially slidable on a guide surface of the projection to facilitate movement between the first and second positions.

4. Dispensing apparatus as claimed in claim 1 wherein the actuator defines a second chamber communicating with the first chamber through a port defined by the valve seat and further defining an outlet nozzle for the release of fluid into the airway, the valve member being located within the second chamber and mounted on a spigot portion of the piston.

5. Dispensing apparatus as claimed in claim 4 wherein the spigot projects into the second chamber through an aperture defined in an end wall of the actuator, the valve member being urged into sealing contact with the end wall to seal the aperture by movement of the piston into the second position.

6. Dispensing apparatus as claimed in claim 5 wherein the valve member comprises a body portion connected to the spigot so as to extend through the aperture in the end wall of the actuator and a head portion making sealing contact with the valve set in the first position of the piston, the head portion being of greater cross-section than the aperture and comprising a peripheral flange operable to make sealing contact with the end wall in the second position of the piston.

7. Dispensing apparatus as claimed in claim 5 wherein the valve member is connected to the spigot by connection means operable to urge the valve member away from the valve seat during motion of the piston from the first position to the second position.

8. Dispensing apparatus as claimed in claim 1 wherein the airway extends through the socket and the housing defines at least one port communicating between the socket and the duct at a location upstream of the piston with respect to the direction of air flow during inhalation.

9. Dispensing apparatus as claimed in claim 8 wherein the housing defines a further chamber forming part of the airway and communicating with the socket, the housing defining at least one further port communicating between the further chamber and the duct at a location upstream of the piston with respect to the direction of air flow during inhalation.

* * * * *